United States Patent [19]

Sih

[11] 4,236,019
[45] Nov. 25, 1980

[54] ESTERS OF PROSTACYCLIN-TYPE COMPOUNDS

[75] Inventor: John C. Sih, Kalamazoo, Mich.

[73] Assignee: The Upjohn Company, Kalamazoo, Mich.

[21] Appl. No.: 48,496

[22] Filed: Jun. 14, 1979

Related U.S. Application Data

[62] Division of Ser. No. 933,329, Aug. 14, 1978, Pat. No. 4,180,657.

[51] Int. Cl.$^3$ .......................................... C07C 177/00
[52] U.S. Cl. .................................................. 560/119
[58] Field of Search ........................................ 560/119

[56] References Cited

PUBLICATIONS

Kojima et al., Tet. Letters, 3743 (1978).

Primary Examiner—Robert Gerstl
Attorney, Agent, or Firm—Robert A. Armitage

[57] ABSTRACT

Acyl-substituted phenyl esters of prostacyclin-type compounds, for example the 4-acetylphenyl ester of prostacyclin (PGI$_2$) illustrated by the formula

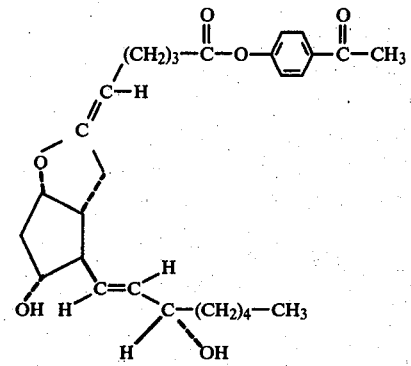

and including esters of the isomeric 6-hydroxy-PGI$_1$ and 6-keto-PGF$_{1\alpha}$ compounds, said esters having pharmacological activity. Processes for preparing them and the appropriate intermediates are disclosed.

2 Claims, No Drawings

ESTERS OF PROSTACYCLIN-TYPE COMPOUNDS

The present application is a divisional application of Ser. No. 933,329, filed Aug. 14, 1978, now issued as U.S. Pat. No. 4,180,657, on Dec. 25, 1979.

The present invention relates to prostaglandin analogs for which the essential material constituting a disclosure therefor is incorporated by reference here from U.S. Pat. No. 4,180,657, issued Dec. 25, 1979.

I claim:

1. An acid ester of a 6a-carba prostacyclin analog of the formula

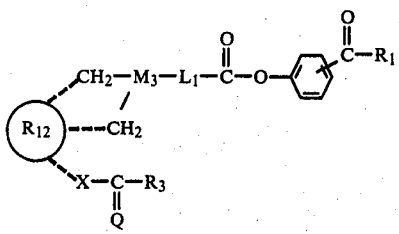

wherein $L_1$ is
(1) $-(CH_2)_n-$ wherein n is one to 5, inclusive,
(2) $-(CH_2)_p-CF_2-$ wherein p is 2, 3, or 4, or
(3) $-(CH_2)_v-CH=CH-$ wherein v is 1, 2, or 3, wherein $M_3$ is

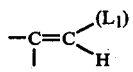 (1)

or

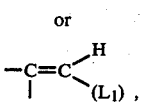 (2), wherein Q is

wherein $R_4$ is hydrogen or alkyl of one to 4 carbon atoms, inclusive, wherein $R_1$ is alkyl of one to 4 carbon atoms with the proviso that when $R_1$ is tert-butyl the group

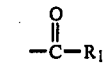

is in the 4-position, wherein $R_3$ is

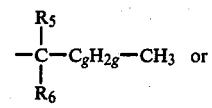

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;

wherein $R_{12}$ is

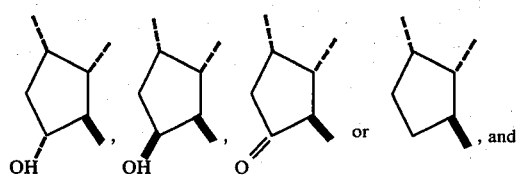

wherein X is
(1) trans-CH=CH—
(2) cis-CH=CH—
(3) —C≡C— or
(4) —CH$_2$CH$_2$—.

2. (5Z and 5E)-6a- Carba-PGI$_2$, 4-acetylphenyl ester, compounds according to claim 1.

* * * * *

UNITED STATES PATENT OFFICE
CERTIFICATE OF CORRECTION

Patent No. 4,236,019              Dated 25 November 1980

Inventor(s) John C. Sih

It is certified that error appears in the above-identified patent and that said Letters Patent are hereby corrected as shown below:

Column 1, line 31, "$-(CH_z)_n$" should read -- $-(CH_2)_n$ --.

Signed and Sealed this

*Fourteenth* Day of *April 1981*

[SEAL]

*Attest:*

RENE D. TEGTMEYER

*Attesting Officer*     *Acting Commissioner of Patents and Trademarks*